United States Patent
Fox et al.

(10) Patent No.: US 8,980,200 B2
(45) Date of Patent: Mar. 17, 2015

(54) CONDENSED GEOMETRY NOZZLE FOR FLOW CYTOMETRY

(71) Applicant: Bio-Rad Laboratories, Inc., Hercules, CA (US)

(72) Inventors: Daniel N. Fox, Bellvue, CO (US); Matthias J. G. Ottenberg, Holmen, WI (US); Kevin P. Raley, Windsor, CO (US); Nathan Michael Gaskill-Fox, Fort Collins, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/923,622

(22) Filed: Jun. 21, 2013

(65) Prior Publication Data

US 2013/0343965 A1    Dec. 26, 2013

Related U.S. Application Data

(60) Provisional application No. 61/663,033, filed on Jun. 22, 2012.

(51) Int. Cl.
*B01L 99/00*   (2010.01)
*B01L 3/00*    (2006.01)
*G01N 15/14*   (2006.01)

(52) U.S. Cl.
CPC ............ *B01L 3/56* (2013.01); *G01N 15/1404* (2013.01); *G01N 2015/1413* (2013.01)
USPC .......................................... 422/508; 422/524

(58) Field of Classification Search
USPC .................................................. 422/508, 524
See application file for complete search history.

(56) References Cited

U.S. PATENT DOCUMENTS

| | | | |
|---|---|---|---|
| 5,819,948 A | 10/1998 | Van den Engh | |
| 5,840,254 A | 11/1998 | Carver, Jr. et al. | |
| 6,133,044 A * | 10/2000 | Van den Engh | 436/177 |
| 6,861,265 B1 | 3/2005 | denEngh | |

* cited by examiner

*Primary Examiner* — Paul Hyun
(74) *Attorney, Agent, or Firm* — William W. Cochran; Cochran Freund & Young LLC

(57) ABSTRACT

Disclosed is a nozzle assembly that is compact in size and that uses plastic tubing as an injection needle. Standard plastic fittings are utilized, which are inexpensive and widely available. The nozzle assembly has a simple construction and can be easily assembled and disassembled in a few minutes by a user. Cleaning and/or replacement of parts is inexpensive. Plastic tubing can be used as an injection needle that has superior qualities over commonly used stainless steel injection needles. Flexure of the injection needle tubing is prevented because of the compact size of the nozzle cavity.

9 Claims, 4 Drawing Sheets

CONDENSED GEOMETRY NOZZLE FOR FLOW CYTOMETRY

CROSS-REFERENCE TO RELATED APPLICATIONS

This application is based upon and claims priority to U.S. provisional application Ser. No. 61/663,033, filed Jun. 22, 2012, entitled "Condensed Geometry Nozzle for Flow Cytometry," which application is specifically incorporated herein by reference for all that it discloses and teaches.

This application is related to U.S. Provisional Patent Application Ser. No. 61/656,934, filed Jun. 7, 2012, by Daniel N. Fox, Susan Hunter, Nathan Michael Gaskill-Fox, Kevin P. Raley and Richard A. Miles, entitled "Automated and Accurate Drop Delay for Flow Cytometry," U.S. Provisional Patent Application Ser. No. 61/659,528, filed Jun. 14, 2012, by Daniel N. Fox and Nathan M. Gaskill-Fox, entitled "Flow Rate Balance, Dynamically Adjustable Sheath Delivery System for Flow Cytometry," U.S. Provisional Patent Application Ser. No. 61/663,030, filed on the same date as the present application, by Nathan M. Gaskill-Fox, Daniel N. Fox and Rodney C. Harris, entitled "Multi-Directional Sorting with Reduced Contamination in a Flow Cytometer," U.S. Provisional Patent Application Ser. No. 61/663,026, filed on the same date of the present application, by National M. Gaskill-Fox, Daniel N. Fox, and Rodney C. Harris, entitled "Two Station Sample and Washing System," and U.S. Provisional Patent Application Ser. No. 61/663,021, filed on the same date as the present application, by Daniel N. Fox and Nathan M. Gaskill-Fox, entitled "Fluid Mixing and Rinsing System for a Flow Cytometer." All of these applications are hereby specifically incorporated herein by reference, for all that they disclose and teach.

BACKGROUND

Flow cytometers are useful devices for analyzing and sorting various types of particles in fluid streams. These cells and particles may be biological or physical samples that are collected for analysis and/or separation. The sample is mixed with a sheath fluid for transporting the particles through the flow cytometer. The particles may comprise biological cells, calibration beads, physical sample particles, or other particles of interest. Sorting and analysis of these particles can provide valuable information to both researchers and clinicians. In addition, sorted particles can be used for various purposes to achieve a wide variety of desired results.

SUMMARY

An embodiment of the present invention may therefore comprise a nozzle assembly for a flow cytometer comprising: a body portion that is formed from a plastic material, the body portion formed to have a nozzle cavity that has a compact size and shape that inhibits the formation of bubbles in a sheath fluid disposed in the cavity; a nozzle tip releasably attached to the body portion and concentrically aligned with the nozzle cavity; a fitting that is releasably attached to the body portion; plastic tubing centrally disposed in the nozzle cavity that extends through the fitting and is secured to the body portion by the fitting; an alignment disk seated in an opening in the body portion that engages the plastic tubing and centers the plastic tubing in the nozzle tip for injection of sample fluids in the nozzle tip; a retainer that releasably secures the nozzle tip and the alignment disk to the body portion.

An embodiment of the present invention may further comprise a method of making a nozzle assembly for a flow cytometer comprising: providing a plastic body portion having a nozzle cavity; inserting a tube fitting into the plastic body portion; inserting an alignment disk into the body portion so that the alignment disk is concentrically aligned with the nozzle cavity; inserting a plastic tube through the tube fitting, the nozzle cavity and the alignment disk; securing and sealing the plastic tube to the body portion by tightening the tube fitting to the body portion; placing a releasable retainer onto the body portion to secure the alignment disk and the nozzle tip to the body portion.

DETAILED DESCRIPTION OF THE EMBODIMENTS

Figure 1:
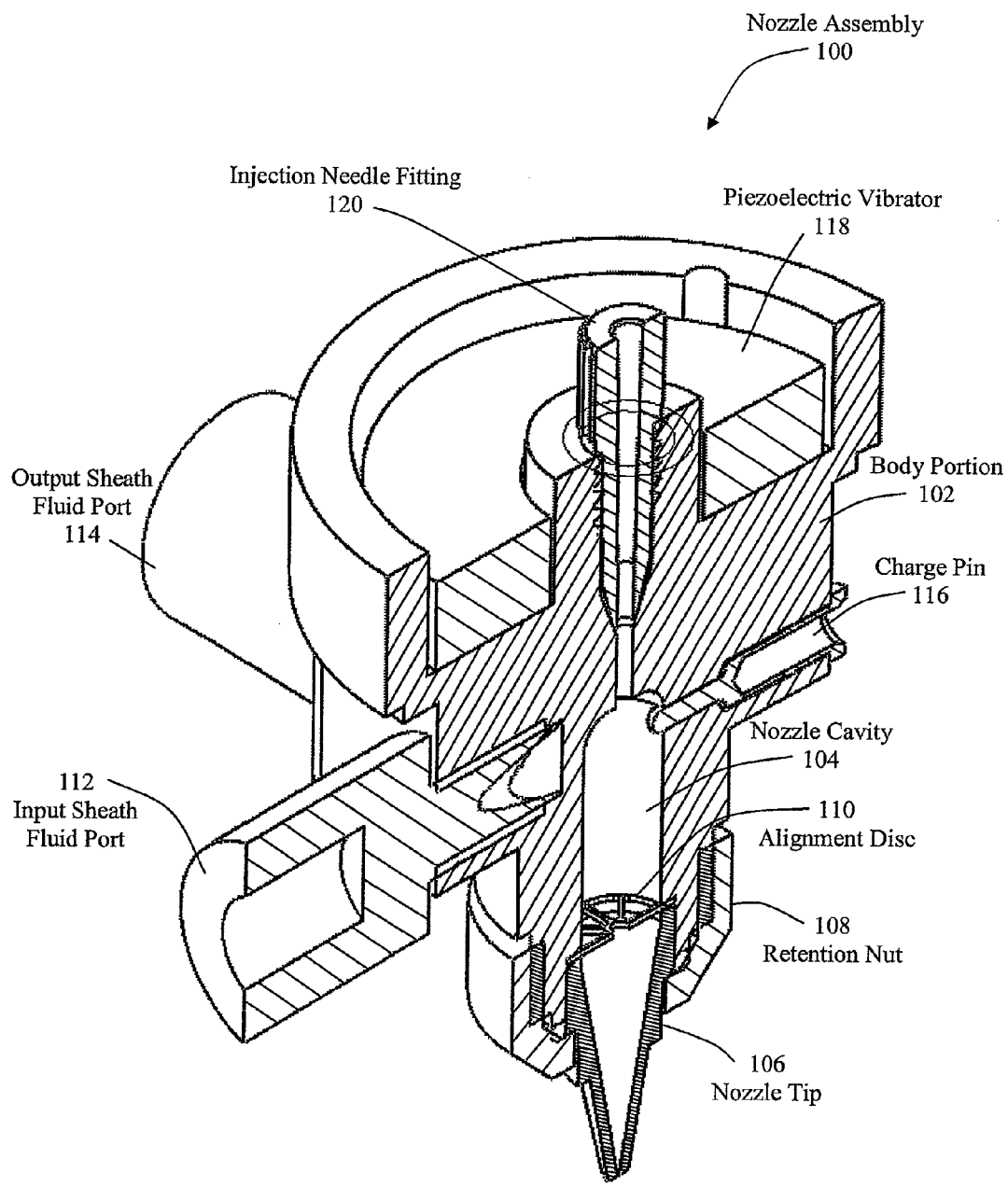
FIG. 1 is a schematic isometric view of a section of a nozzle assembly.

FIG. 1 is an isometric, sectional view of a nozzle assembly 100 that comprises one embodiment of the present invention. As illustrated in FIG. 1, the body portion 102 is made from a single piece of machined or molded plastic, such as polysulfone. Other materials can also be used. The nozzle assembly 100 is used in a flow cytometer for hydrodynamic focusing of a sample fluid in a stream of sheath fluid. In order to ensure that sample particles are properly located in the sheath stream using hydrodynamic focusing, the sample fluid must be injected in a proper direction and at a proper location in the central portion of the flow of sheath fluid. Further, a smooth surface must exist on the interior surface of the injection needle to prevent sample cells from accumulating and plugging the needle. The needle opening is small, on the order of 0.01 inches. Although stainless steel injection needles have been utilized, stainless steel does not provide a sufficiently smooth surface to substantially prevent accumulation of cells, resulting in plugging and contamination of the needle. Processes, such as electro-polishing, for smoothing the interior surface of the stainless steel injection needles do not exist. Also, the stainless steel needles are difficult and expensive to manufacture. Replacement of stainless steel injection needles to prevent contamination is expensive and time consuming.

Plastic injection needles formed from plastic tubing have been used in some instances because they are less expensive and provide an extremely smooth interior surface that is not easily contaminated. In addition, plastic injection needles can be easily and inexpensively replaced. However, the plastic that has typically been used for injection needles, that provides sufficient smoothness, does not have the rigidity that is provided by a stainless steel injection tube to carefully locate and direct the sample stream in the sheath fluid. Also, the internal volume of existing nozzles typically requires that the plastic tubing extend over a distance in an unsupported manner, which can cause flexure of the plastic injection needles, resulting in mislocation and misdirection of the sample fluid exiting the injection needle.

Other factors that can affect proper hydrodynamic focusing of the sample fluid include the generation of air bubbles that form on interior portions of the nozzle cavity in the sheath fluid. Large internal volumes of the nozzle cavity can exacerbate the issues of bubble formation. Some existing devices have internal nozzle volumes of as much as 2.5 mL. Larger cavities tend to enhance the formation of bubbles. In addition, turbulence created in larger cavities can also cause bubble formation. Large cavities may also approach a size where the structural resonances of the nozzle cavity and body themselves may create unwanted regions of droplet formation instability. Although some systems attempt to create turbulence to remove bubbles that adhere to the inner walls of the cavity of the nozzle, such turbulence may also create additional bubbles. Hence, turbulence is an ineffective manner of removing bubbles. Also, the use of additional supports to support flexible plastic injection needles provides additional places for bubbles to form and additional, undesirable turbulence.

As illustrated in FIG. 1, the nozzle assembly 100 has a small nozzle cavity 104 with smooth round surfaces that do not tend to cause bubble formation and that may be well below the structural resonances that can create unwanted regions of droplet formation instability. The nozzle tip 106 is secured to the body portion 102 of the nozzle assembly 100 by a retention nut 108. Disposed between the nozzle tip 106 and the body portion 102 is an alignment disk 110. The body portion 102 is machined plastic, e.g., polysulfone, that is self-centered and self-aligned to ensure proper alignment of all of the various parts of the nozzle assembly 100. The alignment disk 110 is a stainless steel disk that holds the plastic injection needle in a straight orientation at a location that is centered in the nozzle cavity 104. The alignment disk 110 fits within the opening of the nozzle cavity 104 and is centrally aligned to centrally locate the injection needle in the sheath fluid stream. The alignment disk 110 can be easily removed, cleaned and/or replaced, as well as the nozzle tip 106, by simply removing the retention nut 108.

As also shown in FIG. 1, charge pin 116 protrudes into the nozzle cavity 104 to provide a charge to the sheath fluid in the nozzle cavity 104 during operation. In this manner, the sheath fluid in the nozzle cavity 104, as well as the stream exiting the nozzle tip 106, can be charged with a predetermined charge. Input sheath fluid port 112 provides a source of sheath fluid to the nozzle cavity 104. The output sheath fluid port 114 is located near the top surface of the nozzle cavity 104 to remove sheath fluid and bubbles that may form and collect within the nozzle cavity 104. Piezoelectric vibrator 118 provides a resonant vibration to the body portion 102 that causes the stream of fluid exiting the nozzle tip 106 to break off into droplets in a consistent manner. In one embodiment, the piezoelectric vibrator is glued to the body portion 102 with an epoxy glue. Injection needle fitting 120 fits within an upper portion of the body portion 102. The fitting is a standard plastic tube fitting that is threaded into the body portion 102 and compresses the plastic tubing comprising the injection needle to create a seal. Plastic injection needle fitting 120 is inexpensive and provides a solid seal around the injection needle tubing to hold the injection needle tubing in place.

Figure 2:
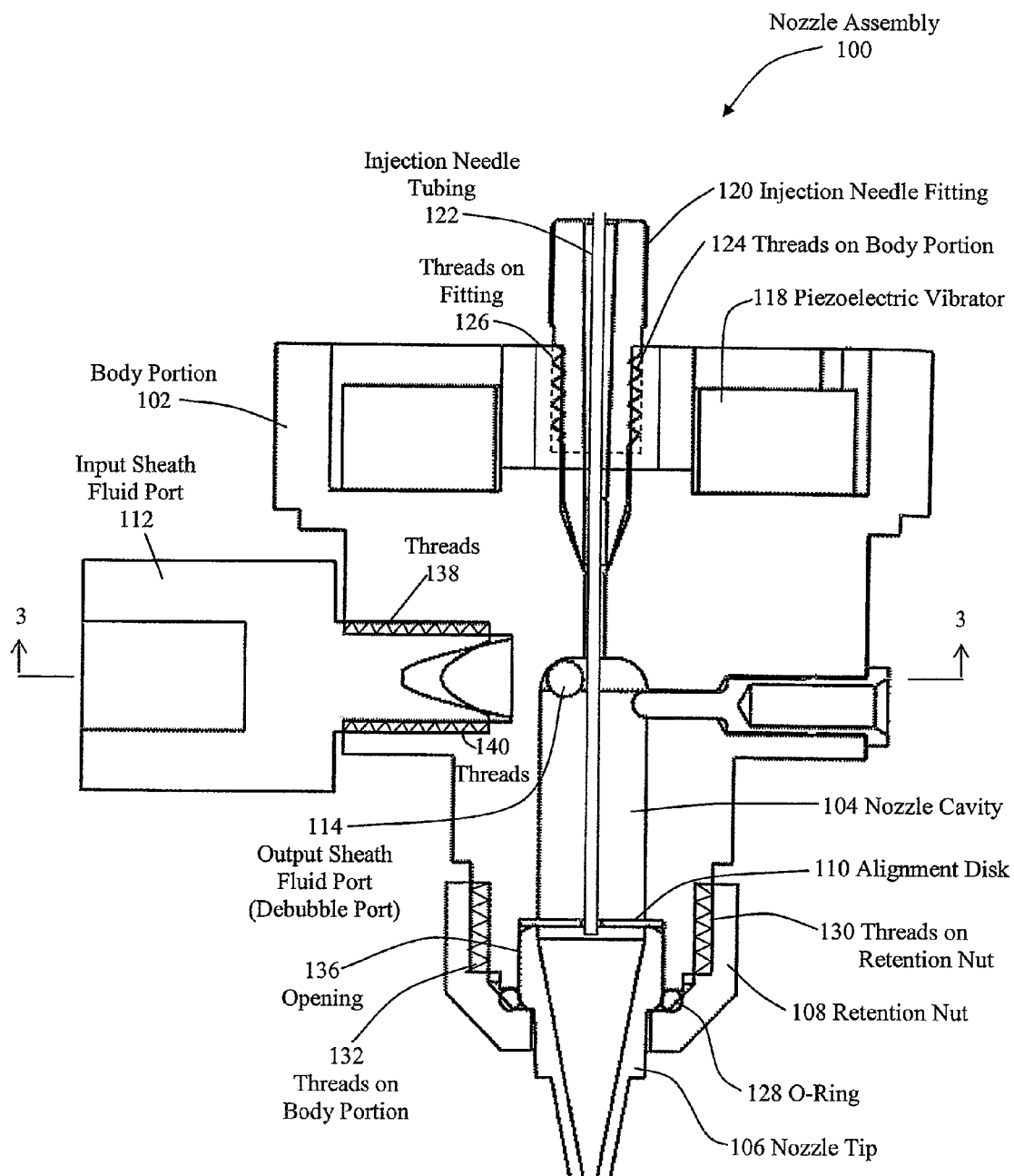
FIG. 2 is a side sectional view of the nozzle assembly of FIG. 1.

FIG. 2 is a side sectional view of the nozzle assembly 100. As illustrated in FIG. 2, the injection needle fitting 120 secures the injection needle tubing 122 in the nozzle assembly 100. The injection needle fitting 120 is a standard tube fitting that both holds and seals the tubing that constitutes the injection needle tubing 122. The injection needle tubing 122 is made from polyether ether ketone (PEEK). The PEEK material is a colorless organic polymer thermoplastic. PEEK is a semicrystaline thermoplastic with excellent mechanical and chemical resistance properties. PEEK is highly resistant to thermal degradation, as well as attack by organic and aqueous solutions. The injection needle tubing 122, in one example, is a 1/32 inch outer diameter and a 0.010 inch inner diameter. The injection needle fitting 120 has threads 124 that engage threads on the body portion 102 that cause the injection needle fitting 120 to compress, hold and provide a seal between the injection needle tubing 122 and the body portion 102. The injection needle tubing 122 extends into the nozzle cavity 104 and through a central opening in the alignment disk 110. Because the length of the nozzle cavity 104 is short, the injection needle tubing 122 remains centered and does not require additional support. Because the injection needle tubing 122 provides an extremely smooth inner surface and has properties that are highly resistant to attack by both organics and aqueous solutions, particles of the sample fluid do not tend to accumulate and clog the injection needle tubing 122. During assembly, the injection needle tubing 122 is simply inserted through the opening in the injection needle fitting 120 and extended down through the nozzle cavity until the injection needle tubing 122 protrudes through the central opening in the alignment disk 110. At that point, the injection needle fitting 120 is rotated to seal the injection needle tubing 122 in the nozzle assembly 100. The injection needle tubing 122 can extend directly to the sample reservoir or may be connected to other tubing. In any event, the assembly of the injection needle tubing 122 in the nozzle assembly 100 is simple and easily carried out. Further, the injection needle tubing 122 provides superior properties, as inexpensive and easily replaceable. The threads 124 in the body portion 102 are machined to engage the threads 126 on the injection needle fitting 120 for easy assembly. The injection needle fitting 120 is a standard tube fitting with standard threading, which is constructed of plastic, is inexpensive and is widely available.

As also illustrated in FIG. 2, the nozzle tip 106 is held in place against the alignment disk 110 by a retention nut 108. O-ring 128 seals the nozzle tip and the retention nut 108 to the body portion 102 of the nozzle assembly 100. During assembly, the alignment disk 110 is inserted in an opening in the lower part of the body portion 102 adjacent the nozzle cavity 104. The alignment disk 110 is centrally aligned with the nozzle cavity 104, since the opening at the bottom part of the body portion 102 is concentric with the nozzle cavity 104. Once the alignment disk 110 is inserted in the opening 136, the injection needle tubing 122 is inserted through the injection needle fitting 120, through the nozzle cavity 104, and through the central opening in the alignment disk 110, until the injection needle tubing 122 extends a small distance through the central opening in the alignment disk 110. Nozzle tip 106 is then inserted in the opening and abuts against the alignment disk 110. Retention nut 108 is then threaded onto the body portion 102. The threads 130 on the retention nut 108 are standard threads that match the threads 132 on the body portion 102. O-ring 128 is disposed on an interior portion of the retention nut 108 and creates a seal between the nozzle tip 106, the body portion 102, and the retention nut 108. Accordingly, assembly of the device can be simply and easily performed, and portions of the device, including the injection needle tubing 122, alignment disk 110 and nozzle tip 106, can be easily removed, cleaned and/or replaced. Similarly, input sheath fluid port 112 has threads 138 that are standard threads that engage threads 140 in the body portion 102. In this manner, the input sheath fluid port 112 can be easily assembled to the body portion 102 and easily removed, if needed.

As illustrated in FIG. 2, the body portion 102 is sufficiently small that vibrations created by the piezoelectric vibrator 118 are efficiently transferred to the sheath fluid and sample fluid in the nozzle tip 106. Epoxy glue that is used to glue the piezoelectric vibrator 118 to the body portion 102 effectively transfers the vibrations and provides a simple and easy manner of mounting the piezoelectric vibrator 118 in the plastic body portion 102. Another advantage of providing a body portion 102 that is made from polysulfone is that polysulfone is substantially clear, so that the nozzle cavity 104 can be viewed during operation of the nozzle assembly 100. As such, bubble formations and the removal of bubble formations in the nozzle cavity 104 by the output sheath fluid port 114 can be observed during operation.

Figure 3:
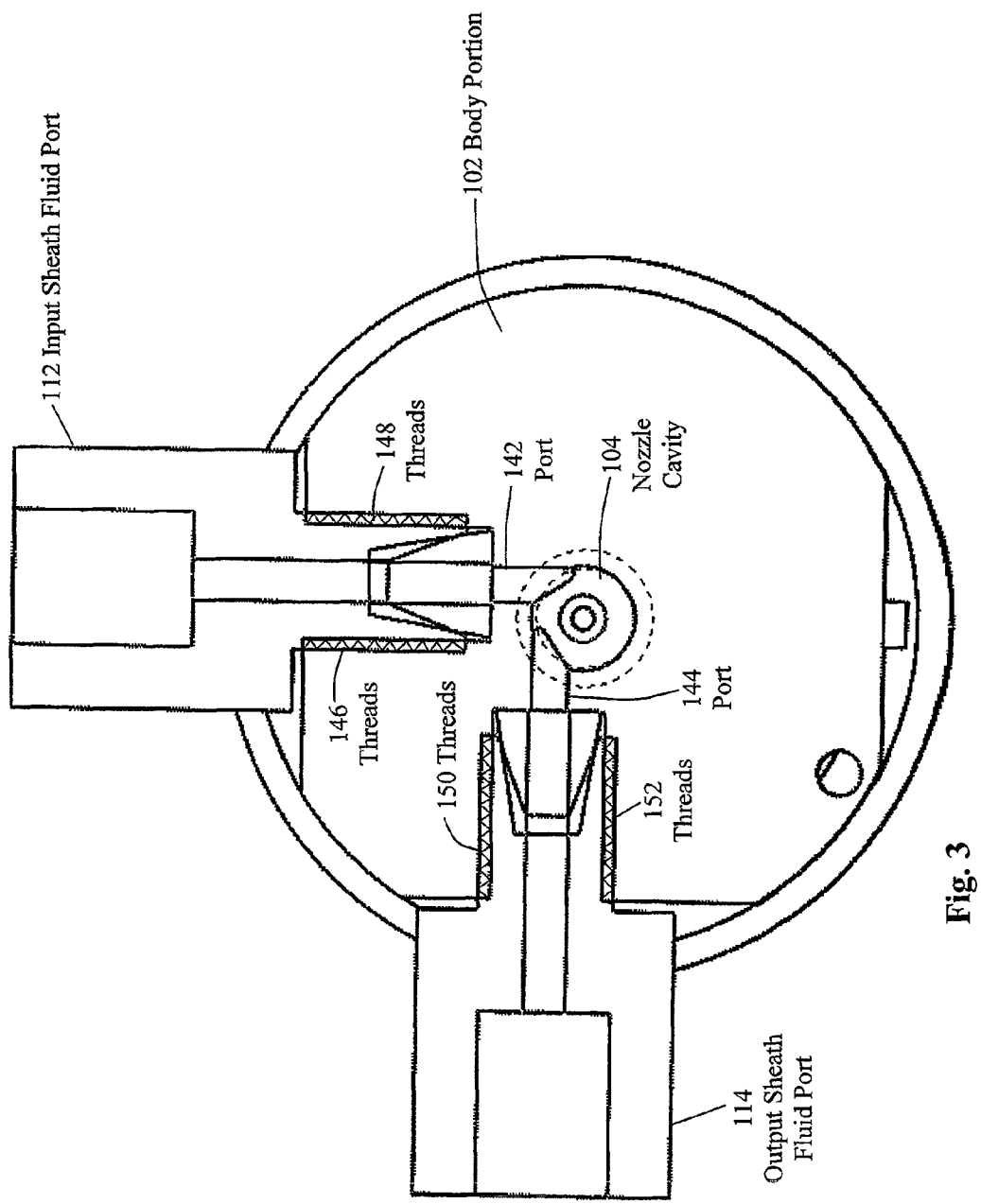
FIG. 3 is a bottom sectional view illustrating portions of the embodiment of the nozzle illustrated in FIGS. 1 and 2.

FIG. 3 is a sectional bottom view of the embodiment of the nozzle assembly 100 illustrated in FIGS. 1 and 2. As shown in FIG. 3, the input sheath fluid port 112 is threaded into the body portion 102. Threads 146 on the input sheath fluid port 112 engage threads 148 formed in the body portion 102. Input sheath fluid port 112 may comprise a standard plastic fitting that is commonly available. Similarly, output sheath fluid port 114 is threaded into the body portion 102. Threads 150 of the output sheath fluid port 114 engage threads 152 formed in the body portion 102. Port 142 that is formed in the body portion 102 is aligned with the opening in the input sheath fluid port 112. Port 142 comprises an opening in the nozzle cavity 104 that is off center in the nozzle cavity 104. The input sheath fluid that is inserted into the nozzle cavity 104, since the port 142 is off center, causes the sheath fluid to swirl in the nozzle cavity 104. The swirling effect tends to remove bubbles that may be lodged on the walls of the nozzle cavity 104, without causing turbulence that may create additional bubbles. Port 144 is formed in the body portion 102 and is aligned with the output sheath fluid port 114. Port 144 is also off center in the nozzle cavity 104 and is aligned at the top of the fluid surface to provide an exit for the swirling fluid to remove the bubbles at the top portion of the sheath fluid in the nozzle cavity 104.

Figure 4:
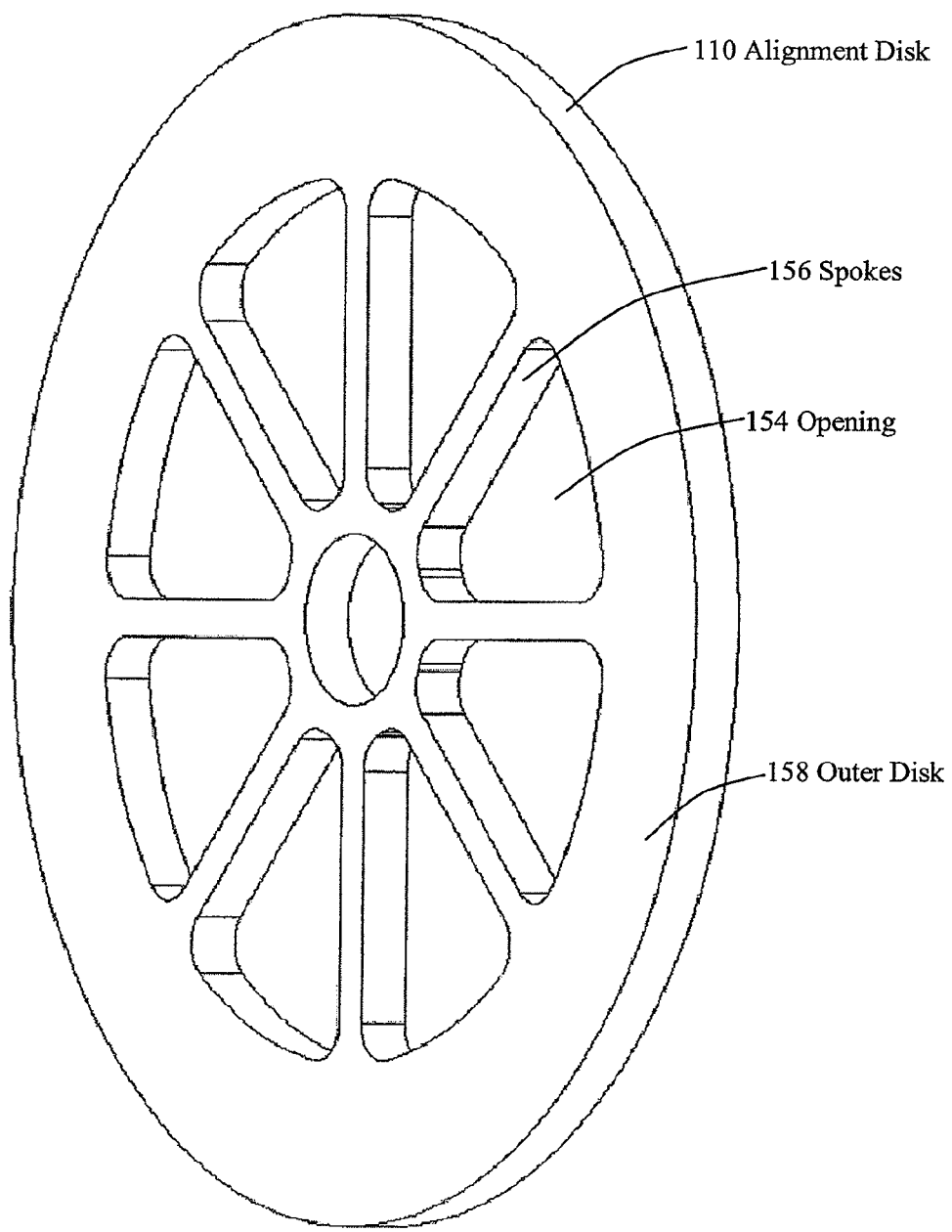
FIG. 4 is an isometric view of the alignment disk.

FIG. 4 is a schematic isometric diagram of alignment disk 110. As shown in FIG. 4, the alignment disk 110 has a series of openings, such as opening 154, that are located between the spokes 156. Openings 154 allow the sheath fluid to flow through the alignment disk 110 from the nozzle cavity 104 into the nozzle tip 106. Outer disk 158 abuts against the body portion 102 in the opening 136. Nozzle tip 106 asserts pressure against the outer disk 158 to hold the alignment disk 110 in a secure position and centrally aligned in the nozzle cavity 104. The alignment disk 110 can be produces via photochemical etching from a sheet of stainless steel metal in a simple and inexpensive manner.

Hence, the nozzle assembly 100 is an embodiment that can be simple and easy to manufacture and assemble, with inexpensive parts. In addition, these parts can be disassembled for cleaning or replacement in a simple and easy manner. The injection needle tubing 122 is inexpensive and easily replaceable. The injection needle tubing 122 can be made from a material such as PEEK, that provides superior qualities, that does not result in clogging or contamination during sorting. Nozzle assembly 100 has a body portion that is a compact size that allows for efficient transmission of vibrations from the piezoelectric vibrator, has a small nozzle cavity 104 that tends to create fewer bubbles in the sheath fluid and does not result in substantial deflection of the injection needle tubing 122, utilizes standard plastic fittings that are inexpensive and widely available, and is designed in a way that allows a user to easily assemble and disassemble. Further, the body portion 102 is made from polysulfone, which is clear, so that the operator can view the operation of the fluid flowing through the nozzle cavity 104.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A nozzle assembly for a flow cytometer comprising:
a body portion that is formed from a plastic material, said body portion formed to have a nozzle cavity that has a compact size and shape that inhibits the formation of bubbles in a sheath fluid disposed in said cavity;
an input sheath fluid port and an output sheath fluid port that are connected at off center positions to said nozzle cavity to create swirling of said sheath fluid in said nozzle cavity;
a nozzle tip releasably attached to said body portion and concentrically aligned with said nozzle cavity;
a fitting that is releasably attached to said body portion;
plastic tubing centrally disposed in said nozzle cavity, said plastic tubing extending through said fitting and secured to said body portion by said fitting;
an alignment disk seated in an opening in said body portion, said alignment disk engaging said plastic tubing and centering said plastic tubing in said nozzle tip for injection of sample fluids in said nozzle tip;
a retainer that releasably secures said nozzle tip and said alignment disk to said body portion.

2. The nozzle assembly of claim 1 wherein said retainer is a threaded retainer nut that is threaded onto said body portion.

3. The nozzle assembly of claim 2 wherein said fitting is a threaded plastic fitting that engages threads in said body portion to secure and seal said plastic tubing to said body portion by tightening said fitting in said body portion.

4. The nozzle assembly of claim 3 further comprising:
an o-ring disposed on said retainer nut that seals said nozzle tip to said body portion.

5. The nozzle assembly of claim 1 wherein said nozzle cavity has a length that is sufficiently short that said plastic tubing does not substantially bend in said nozzle cavity.

6. A method of making a nozzle assembly for a flow cytometer comprising:
providing a plastic body portion having a nozzle cavity;
inserting a tube fitting into said plastic body portion;
inserting an alignment disk into said body portion so that said alignment disk is concentrically aligned with said nozzle cavity;
inserting a plastic tube through said tube fitting, said nozzle cavity and said alignment disk;
threading said tube fitting in a threaded opening of said body portion, said tube fitting compressing and sealing said plastic tubing so that said plastic tubing is sealed with respect to said body portion;
securing and sealing said plastic tube to said body portion by tightening said tube fitting to said body portion;
placing a releasable retainer onto said body portion to secure said alignment disk and a nozzle tip to said body portion.

7. The method of claim 6 further comprising:
placing an o-ring in said retainer to seal said nozzle tip to said body portion.

8. The method of claim 7 wherein said process of placing said releasable retainer on said body portion comprises:

threading a retainer nut onto threads formed on said body portion.

9. The method of claim 8 wherein said process of providing a plastic body portion having a nozzle cavity comprises providing a plastic body portion having a nozzle cavity that has a length that is sufficiently short that said plastic tube that is inserted through said nozzle cavity does not substantially bend.

\* \* \* \* \*